(12) United States Patent
Berg et al.

(10) Patent No.: US 9,278,916 B2
(45) Date of Patent: Mar. 8, 2016

(54) PREPARATION OF PET PRECURSOR

(75) Inventors: Tom Christian Berg, Oslo (NO); Anne Nilsen, Oslo (NO)

(73) Assignee: GE Healthcare Limited, Buckinghamshire (GB)

( * ) Notice: Subject to any disclaimer, the term of this patent is extended or adjusted under 35 U.S.C. 154(b) by 0 days.

(21) Appl. No.: 13/989,527

(22) PCT Filed: Nov. 28, 2011

(86) PCT No.: PCT/EP2011/071145
§ 371 (c)(1),
(2), (4) Date: May 24, 2013

(87) PCT Pub. No.: WO2012/072567
PCT Pub. Date: Jun. 7, 2012

(65) Prior Publication Data
US 2013/0245307 A1    Sep. 19, 2013

Related U.S. Application Data

(60) Provisional application No. 61/417,490, filed on Nov. 29, 2010.

(51) Int. Cl.
| | | |
|---|---|---|
| *C07C 261/00* | (2006.01) | |
| *C07C 269/04* | (2006.01) | |
| *C07B 59/00* | (2006.01) | |
| *C07C 269/08* | (2006.01) | |

(52) U.S. Cl.
CPC ............. *C07C 269/04* (2013.01); *C07B 59/001* (2013.01); *C07C 269/08* (2013.01); *C07C 2101/04* (2013.01)

(58) Field of Classification Search
CPC    C07C 269/08; C07C 2101/04; C07C 271/24; C07C 269/04; C07B 59/001
USPC ............................................................ 560/27
See application file for complete search history.

(56) References Cited

U.S. PATENT DOCUMENTS

| 8,563,771 B2 | 10/2013 | Toyama et al. | |
|---|---|---|---|
| 2008/0281121 A1* | 11/2008 | Ito et al. | ......................... 560/123 |
| 2009/0198085 A1 | 8/2009 | Hayashi et al. | |

FOREIGN PATENT DOCUMENTS

JP       11-302244       11/1999

OTHER PUBLICATIONS

PCT/EP2011/071145 ISRWO Dated Mar. 12, 2012.

* cited by examiner

*Primary Examiner* — Yevegeny Valenrod
*Assistant Examiner* — Blaine G Doletski
(74) *Attorney, Agent, or Firm* — Parks Wood LLC

(57) ABSTRACT

The invention relates to a process for preparation of radiopharmaceutical precursors, and in particular protected amino acid derivatives which are used as precursors for production of radiolabeled amino acids for use in in vivo imaging procedures such as positron emission tomography (PET). Particularly, the invention relates to a process for preparation of a precursor of the [$^{18}$F]-1-amino-3-fluorocyclobutanecarboxylic acid ([$^{18}$F] FACBC) PET agent and particularly to the work-up process of this precursor removing generated salts from the intermediate composition.

15 Claims, No Drawings

PREPARATION OF PET PRECURSOR

This application is a filing under 35 U.S.C. 371 of international application number PCT/EP2011/071145, filed Nov. 28, 2011, which claims priority to U.S. application No. 61/417,490 filed Nov. 29, 2010, the entire disclosure of which is hereby incorporated by reference.

The invention relates to a process for preparation of radiopharmaceutical precursors, and in particular protected amino acid derivatives which are used as precursors for production of radiolabelled amino acids for use in in vivo imaging procedures such as positron emission tomography (PET). Particularly, the invention relates to a process for preparation of a precursor of the [$^{18}$F]-1-amino-3-fluorocyclobutanecarboxylic acid ([$^{18}$F] FACBC) PET agent and specifically to the work up of this precursor.

PET is effective in diagnosing a variety of diseases including heart diseases and cancer. Nuclear medicine imaging methods involve administering an agent labelled with a suitable radioisotope (a "radiopharmaceutical") to a patient, followed by detecting γ-rays emitted directly or indirectly from the agent. These imaging methods are advantageous over other in vivo imaging methods in that as well as being highly specific and sensitive to diseases, they also provide information on the functionality of lesions. For example, the PET radiopharmaceutical [$^{18}$F]2-fluoro-2-deoxy-D-glucose ([$^{18}$F]FDG) concentrates in areas of glucose metabolism, thereby making it possible to specifically detect tumours in which glucose metabolism is enhanced. Nuclear medicine examination is performed by tracing a distribution of an administered radiopharmaceutical, and data obtained therefrom vary depending on nature of the radiopharmaceutical. Thus, different radiopharmaceuticals have been developed for a variety of applications, e.g. tumour diagnostic agents, bloodstream diagnostic agents and receptor mapping agents.

In recent years, a series of radioactive halogen-labelled amino acid compounds including [$^{18}$F]-1-amino-3-fluorocyclobutanecarboxylic acid ([$^{18}$F]FACBC) have been designed as novel radiopharmaceuticals. [$^{18}$F]FACBC is considered to be effective as a diagnostic agent for highly proliferative tumours, because it has a property of being taken up specifically by amino acid transporters.

EP1978015 (A1) provides precursors for the [$^{18}$F]FACBC compound and processes for producing this in a small scale. Scheme 1 shows the synthesis, as outlined in EP1978015, for preparation of [$^{18}$F] FACBC:

Scheme 1

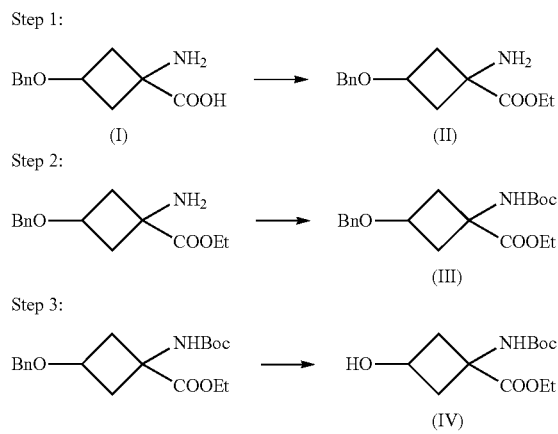

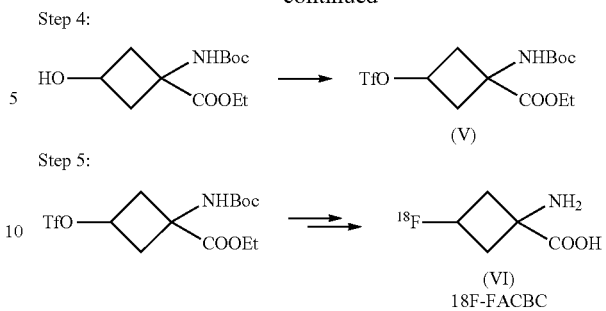

In Scheme 1 above, BnO denotes Benzyl ether, Boc denotes tert-butyl carbamate, and OTf denotes trifluoromethanesulfonate.

The synthesis of [$^{18}$F]FACBC on an automated synthesiser unit is based on nucleophilic displacement of a triflate group by [$^{18}$F]fluoride from the precursor of formula V. The [$^{18}$F] fluoride may be introduced with a solution of kryptofix (K222), potassium carbonate, water and acetonitrile into the reaction vessel. The $^{18}$F-labelled intermediate compound then undergoes two deprotecting steps, where the ethyl and the Boc protecting groups are removed by basic and acidic hydrolysis, respectively.

The compound of formula III:

is named 1-(N-(t-butoxycarbonyl)amino)-3-benzyloxy-cyclobutane-1-carboxylic acid ethyl ester. In accordance with Scheme 1 this compound is prepared in a multi-step synthesis from the syn enantiomer of hydantoin. In the work-up of this intermediate ethyl acetate and hydrochloric acid are added to the resulting composition before the organic layer is extracted and washed with water. In this process of preparing the compound of formula III salts are generated. Such large amounts of salts are generated that these have to be removed before the next steps. When the reactions according to step 1 and 2 of Scheme 1 were performed in larger scale, such as in a commercial scale, e.g. preparing up to 500 grams of the compound of formula III, significant problems were observed. Addition of HCl and ethyl acetate to the crude reaction forms an emulsion when performed at a larger scale and the desired bi-phasic system is not formed. Removal of generated salts using filtration was also not possible when preparing at such a large scale as the filter was totally clogged.

Therefore, there is a need for a work-up process for preparing the compound of formula III on a large scale that overcomes these problems.

It has now surprisingly been found that the problem is avoided if to the crude compound of formula III ethyl acetate is added to form a suspension comprising the majority of inorganic salts in addition to the compound of formula III. Further, the addition of water to the suspension forms a biphasic system that will hold the product in the organic phase and the residual salts in the aqueous phase. Separation of the two phases results in retention of the compound of formula III in the organic phase while the inorganic salts are discarded with the aqueous phase.

The compound of formula III has a very poor solubility in the aqueous phase due to its lipophilic character, thus no significant loss of the compound is observed when the process of the invention is used for purifying this compound.

Therefore, in a first aspect the invention provides of work-up process for preparing a compound of formula IIIa:

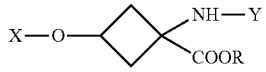
(IIIa)

wherein:

R denotes an alkyl group with 1 to 5 carbon atoms;

X denotes a protecting group for an alcohol;

Y denotes a protecting group for an amine, and wherein the process comprises a work-up process comprising the steps of:

i) providing a crude reaction product comprising said compound of formula IIIa;

ii) adding ethyl acetate to the crude reaction product of step i) to prepare a suspension;

iii) adding water to the suspension of step ii) to form a biphasic system comprising an aqueous phase and an organic phase, and discarding the aqueous phase;

iv) adding an acid to the organic phase of step iii) to form a biphasic system comprising an acidic aqueous phase and an organic phase, and discarding the acidic aqueous phase;

v) washing the organic phase of step iv) with water.

The steps are preferably done in the order as provided above.

The term "work-up process" takes its ordinary meaning in the art and refers to a series of manipulations required to isolate and purify the product of a chemical reaction. In the case of the present invention the product of the chemical reaction is the compound of formula IIIa as defined herein.

The term "alkyl", alone or in combination, means a straight-chain or branched-chain alkyl radical having the general formula $CH_nH_{2n+1}$. Examples of such radicals include methyl, ethyl, and isopropyl.

The term "protecting group" is well-known to those skilled in the art. A protecting group is introduced into a molecule by chemical modification of a functional group in order to obtain chemoselectivity in a subsequent chemical reaction. The use of protecting groups is described in 'Protective Groups in Organic Synthesis', Theorodora W. Greene and Peter G. M. Wuts, (Fourth Edition, John Wiley & Sons, 2007).

The term "alcohol" herein refers to a substituent comprising the group —OH.

The term "amine" herein refers to the group —NR'R" wherein R' and R" are independently hydrogen or an alkyl, and are preferably both hydrogen.

The term "crude reaction product" herein refers to the product of a chemical reaction before any steps of a work-up process have been carried out, wherein the term work-up process is as defined above. Specifically, in the context of the present invention the crude reaction product refers to the product of the chemical reactions (analogous to steps 1 and 2 of Scheme 1 above) carried out to add Y and R to a compound of formula Ia. These steps are illustrated below as steps 1a and 2a:

Step 1a:

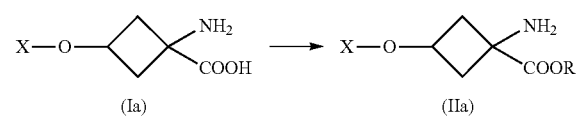

Step 2a:

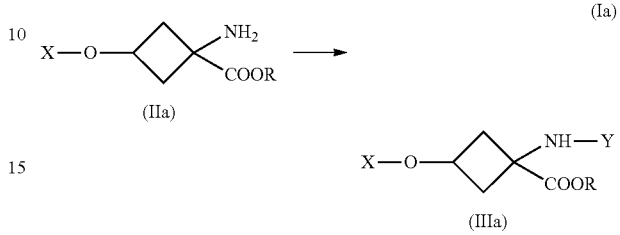

wherein in each case X, R and Y are as defined herein for formula IIIa.

Step (i) of "providing" said crude reaction product comprises step 2a as illustrated above, and this step is described for the specific compound of formula III in Example 1. This step comprises reaction of the compound of formula IIa with a protecting agent for the amine. The crude reaction product comprising a compound of formula IIIa comprises salts.

The term "salt" is well-known to the person skilled in the art and refers to ionic compounds that result from the neutralisation of an acid and a base. When preparing the compound of formula IIIa, such as the compound of formula (III), salts are generated from the reagents and intermediates of the process. Such salts are likely to include different chloride-containing salts, such as thionyl chloride, but this depends on which specific reagents and protecting groups are used.

The term "suspension" takes its ordinary meaning in the art of chemistry, which is a heterogeneous fluid containing solid particles large enough to sediment. The solid particles in the suspension of the present invention are created by addition of the ethyl acetate in step ii), which acts to precipitate out the salts.

The term "biphasic system" used in steps (iii) and (iv) refers to a two-phase system comprising an aqueous phase and an organic phase. The term "aqueous phase" used in step (iii) refers to a phase comprising water as the solvent and the water-soluble components of the biphasic system. The "organicphase" used in steps (iii) and (iv) refers to the phase comprising ethyl acetate and the components of the biphasic system soluble therein. The term "acidic aqueous phase" used in step (iv) refers to the phase of the biphasic system comprising the acid and the components of the biphasic system of step iv that are soluble therein.

The "acid" of step (iv) is an inorganic acid, and should be selected such that it does not affect the protecting groups X and Y. The acid is preferably hydrochloric acid (HCl), or other inorganic acid providing the same pKa.

The moiety R is a linear or branched alkyl chain, and is preferably an alkyl group selected from methyl, ethyl, 1-propyl or isopropyl, and is most preferably ethyl.

The X moiety is a protecting group for alcohol, the protecting group is chosen so that the protecting group forms its related ether, such as; benzyl (Bn), methoxymethyl (MOM), 2-methoxyethoxymethyl (MEM), methylthiomethyl (MTM), tetrahydropyranyl (THP), benzyloxymethyl (BOM), p-Methoxyphenyl, p-methoxybenzyl (MPM), p-methoxybenzyloxymethyl (PMBM), triisopropylsilyl (TIPS), tert-butyldimethylsilyl (TBDMS), 2-(trimethylsilyl)ethoxymethyl (SEM) and (phenyldimethylsilyl)methoxymethyl (SMOM).

A group that can be removed by hydrogenation is preferred and in a preferred embodiment X is benzyl.

The Y moiety is a protecting group for an amine, such as a carbamate. Preferably Y is selected from; tert-butyl carbamate (Boc), 9-fluoroenylmethyl carbamate (Fmoc), methyl carbamate, ethyl carbamate, 2-chloro-3-indenylmethyl carbamate (Climoc), benz[f]inden-3-ylmethyl carbamate (Bimoc), 2,2,2-trichloroethyl carbamate (Troc), 2-chloroethyl carbamate, 1,1-dimethyl-2,2-dibromoethyl carbamate (DB-t-BOC), 1,1-dimethyl-2,2,2-trichloroethyl carbamate (TCBOC), benzyl carbamate (Cbz) and diphenylmethyl carbamate. Most preferably Y is tert-butyl carbamate, to provide N-tert-butoxycarbonyl.

In a particularly preferred embodiment R is an ethyl group, X is benzyl and Y is Boc such that the compound of formula IIIa is a compound of formula III.

In step (ii) of the process ethyl acetate is added to the composition comprising the crude compound of formula IIIa. The amount of ethyl acetate added compared to the amount of the starting material for the reaction to prepare the crude compound of formula IIIa is e.g. between 15:1 and 25:1, more preferably between 18:1 and 21:1, in volume/weight %. In a preferred embodiment the starting material is defined as a composition comprising the compound of formula IIa. Such composition would also include salts. When ethyl acetate is added, a suspension is formed. No acid is added in this step. If acid is added at this stage as described in EP1978015 an emulsion would be formed when carried out on a larger scale.

In step (iii) water is added to the suspension of step (ii) to remove salts. The problems associated with the salt generation are avoided if the crude compound of formula IIIa is added water to ensure that the majority of inorganic salts are dissolved in the aqueous phase, and that the salts are transferred into the aqueous phase, which is discarded. The compound of formula IIIa will stay in the organic phase, without the salts present, and this phase will continue in the work-up process. The amount of water added in step (iii) compared to the amount of the starting material for the reaction to prepare the crude compound of formula IIIa is e.g. between 5:1 and 15:1, more preferably between 9:1 and 10:1, in volume/weight %. Most preferably, the amount of water added in step (iii) is about half the amount of ethyl acetate added in step (ii).

In step (iv) an acid is added to the organic phase of step (iii). When the acid is added another phase separation occurs, and a biphasic system comprising an organic phase and an acidic aqueous phase is formed. The aqueous phase is discarded while the organic phase continues in the work-up process. The function of the acid is to protonate the target compound of formula IIIa, to avoid that this compound exists as an anion type of compound that would be extracted into the aqueous phase. The amount of acid is preferably about the same amount as the amount of ethyl acetate added in step (ii), and the strength is e.g. 0.2-0.8 Molar, and most preferably 0.5 Molar.

In step (v) the organic phase from step (iv) including the compound of formula IIIa is washed with water, preferably several times. This washing step may include the washing with pure water, with aqueous solutions of sodium hydrogen carbonate and with brine. Preferably, this step includes the steps of washing with water twice, followed by washing with an aqueous solution of sodium hydrogen carbonate, followed with washing with water again, before washing with brine. Each washing with water is preferably done twice. In a preferred embodiment, this washing step (v) includes several steps of washing, each time with a given aqueous amount, preferably with water twice, with an aqueous solution of sodium hydrogen carbonate, with water again, and then with brine. The given aqueous amount is preferably the same for all these steps, and the aqueous amount is preferably the same amount as the amount of water added in step (iii).

In the work-up process of the invention, each separation of an organic phase and an aqueous phase is done by extraction.

After step (v) optional additional steps include concentrating the composition from step (v) such as under reduced pressure, drying this, such as with a suitable drying agent, and purifying e.g. by flash chromatography on a silica gel column. In a preferred embodiment, the compound of formula III is prepared according to this process.

The process of the invention is particularly useful when preparing in large scale, such as when preparing 100 grams or more, such as 300 grams, or up to 500 grams or more, of the compound of formula IIIa. In smaller scales, the generated salts may be removed by filtering, but when scaling up, it was experienced that it was impossible to remove the salts by filtering due to clogging of the filters. The process of the invention including washing out the salts has been found much simpler and more efficient and cost efficient. When scaling up it was further found that the process is much less time consuming than a process including filtering off the generated salts. It is expected that 2-4 days are saved when using the process of the invention in large scale, compared to using a process including filtering off salts, if at all possible. If trying to use a process including filtering off the salts, in large scale, expensive equipment for large scale filtering would be needed.

In a preferred embodiment, the starting composition for the work-up process of the invention, i.e. the composition comprising crude compound IIIa, includes a mixture of the syn- and anti-enantiomer of the compound IIIa, and more particularly a compound of formula III. Hence, in a preferred embodiment the starting reagent for the process of Scheme 1 is a mixture of the syn- and anti-enantiomer of the hydantion of formula 0:

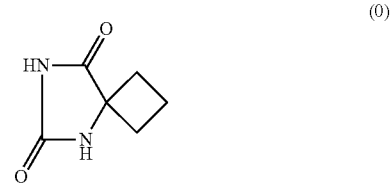

(0)

which is 5-(3-benzyloxycyclobutane)hydantoin.

When using the process of the invention, it has been found that there is no need for actively separating enantiomers, at any stage of the process for preparing the precursor for $^{18}$F-FACBC named compound V in Scheme 1.

In a further aspect, the invention provides a process for preparing the compound of formula Va:

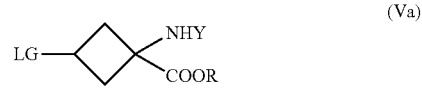

(Va)

wherein Y and R are as suitably and preferably defined herein for formula IIIa, and LG is a leaving group;
wherein said process comprises preparing the compound of formula IIIa according to the process as suitably and preferably defined herein.

The leaving group LG is preferably a halogen substituent or a group represented by —$OR^2$ wherein $R^2$ is either a fluorosulfonic acid substituent or an aromatic sulfonic acid substituent. Most preferably the leaving group is selected from a toluenesulfonic acid substituent, a nitrobenzenesulfonic acid substituent, a benzenesulfonic acid substituent, a trifluoromethanesulfonic acid substituent, a fluorosulfonic acid substituent, or a perfluoroalkylsulfonic acid substituent.

The compound of formula Va is preferably a compound of formula V:

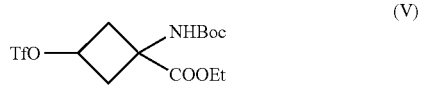 [SMILES: CCOC(=O)C1(NC(=O)OC(C)(C)C)CC(OS(=O)(=O)C(F)(F)F)C1]

which is a direct labeling precursor compound for $^{18}$F-FACBC. OTf denotes trifluoromethanesulfonate. Y in formula IIa is then Boc and R is ethyl.

In a yet further embodiment, the present invention provides a process for preparing a compound of formula VI:

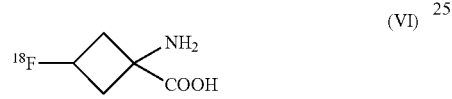

wherein said process comprises preparing the compound of formula IIIa according to the process as suitably and preferably defined herein.

The invention is illustrated by way of the example below.

EXAMPLE 1

Synthesis and purification of 1-(N-(t-butoxycarbonyl)amino)-3-benzyloxy-cyclobutane-1-carboxylic acid ethyl ester (compound of formula (III))

Synthesis:

1-amino-3-benzyloxycyclobutane-1-carboxylic acid ethyl ester (compound of formula II) (630 g, included salt residues from previous step) was stirred in ethanol (18500 ml) and triethylamine (2000 ml) under an $N_2$-atmosphere and was cooled to <5° C. The cooled solution was added tert-butyl dicarbonate (602 g), and the resulting mixture was allowed to come to ambient temperature and stirred for 20 hours while the reaction progress was monitored by TLC analysis. Upon complete reaction the mixture was evaporated in vacuo to dryness at 35° C.

Purification:

The crude product from the synthesis above, including the compound of formula III and salts, was added ethyl acetate (12000 ml) to afford a suspension, and water (6000 ml) was added the suspension to form a biphasic system. The phases were separated and the water phase was discarded. The organic phase was washed with HCl (12000 ml, 0.5 M) and the acidic aqueous phase was discarded. The organic phase was washed with water (6000 ml, ×2), followed by a sodium hydrogen carbonate solution (6000 ml), water (6000 ml) and brine (6000 ml, ×2), and the organic phase was dried over sodium sulfate anhydride, filtered and evaporated in vacuo, to provide the title compound.

What is claimed is:

1. A process for preparing a compound of formula IIIa:

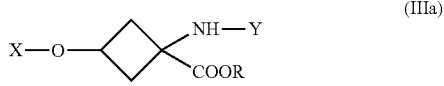

wherein:
R denotes an alkyl group with 1 to 5 carbon atoms;
X denotes a protecting group for an alcohol;
Y denotes a protecting group for an amine, and
wherein the process comprises a work-up process comprising the steps of:
  i) providing at least 100 grams of a crude reaction product comprising said compound of formula IIIa and salts;
  ii) adding ethyl acetate to the crude reaction product of step i) to prepare a suspension;
  iii) adding a liquid that consists of water to the suspension of step ii) to form a biphasic system comprising an aqueous phase containing the salts, and an organic phase, and discarding the aqueous phase and the salts;
  iv) adding an acid to the organic phase of step iii) to form a biphasic system comprising an acidic aqueous phase and an organic phase, and discarding the acidic aqueous phase;
  v) washing the organic phase of step iv) with water.

2. A process as claimed in claim 1 wherein X is benzyl.

3. A process as claimed in claim 1 wherein R is ethyl.

4. A process as claimed in claim 1 wherein Y is tert-butyl carbamate (Boc).

5. A process as claimed in claim 1 wherein in step ii) the amount of ethyl acetate added compared to the amount of a starting material comprising a compound of formula IIa:

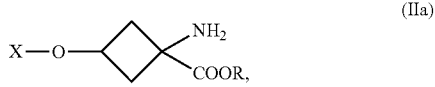

wherein X and R are defined as in claim 1;
is between 15:1 and 25:1 in volume/weight %.

6. A process as claimed in claim 1 wherein in step iii) the amount of water added is about half the amount of ethyl acetate added in step ii).

7. A process as claimed in claim 1 wherein in step iv) the acid added is HCl.

8. A process as claimed in claim 1 wherein in step v) the washing with water is followed by several steps of washing including washing with an aqueous solution of sodium hydrogen carbonate, optionally washing with water again, and washing with brine.

9. A process as claimed in claim 1 further including the steps of concentrating the composition from step iv) under reduced pressure, drying and purifying.

10. A process as claimed in claim 1 wherein the crude reaction product includes a mixture of the syn- and anti-enantiomer of the compound of formula IIIa.

11. A process for preparing the compound of formula Va:

wherein Y is as defined in claim 1 and R is as defined in claim 1, and LG is a leaving group; wherein said process comprises preparing the compound of formula IIIa according to the process of claim 1.

12. A process as defined in claim 11 wherein said leaving group is a halogen substituent or a group represented by —OR² wherein R² is either a fluorosulfonic acid substituent or an aromatic sulfonic acid substituent.

13. A process as defined in claim 12 wherein said leaving group is selected from a toluenesulfonic acid substituent, a nitrobenzenesulfonic acid substituent, a benzenesulfonic acid substituent, a trifluoromethanesulfonic acid substituent, a fluorosulfonic acid substituent, or a perfluoroalkylsulfonic acid substituent.

14. A process as defined in claim 11 wherein said compound of formula Va is a compound of formula V:

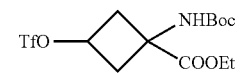

(V)

15. A process for preparing a compound of formula VI:

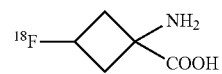

(VI)

wherein said process comprises preparing the compound of formula IIIa according to the process as defined in claim 1 wherein Y is as defined in claim 1.

* * * * *